United States Patent [19]

Wong

[11] Patent Number: 5,102,844
[45] Date of Patent: Apr. 7, 1992

[54] POLYMERIZATION PROCESS

[75] Inventor: Pui K. Wong, Katy, Tex.

[73] Assignee: Shell Oil Company, Houston, Tex.

[21] Appl. No.: 706,496

[22] Filed: May 28, 1991

Related U.S. Application Data

[62] Division of Ser. No. 503,414, Mar. 30, 1990, Pat. No. 5,057,599.

[30] Foreign Application Priority Data

Jul. 14, 1989 [NL] Netherlands .......................... 8901829

[51] Int. Cl.$^5$ .............................................. B01J 31/24
[52] U.S. Cl. ................................... 502/162; 502/165; 502/167
[58] Field of Search .................... 502/162, 165, 167

[56] References Cited

U.S. PATENT DOCUMENTS

| | | | |
|---|---|---|---|
| 2,495,286 | 1/1950 | Brubaker | 260/63 |
| 3,694,412 | 9/1972 | Nozaki | 260/63 |
| 4,818,810 | 4/1989 | Drent | 528/392 |
| 4,835,250 | 5/1989 | Drent | 528/392 |
| 4,843,144 | 6/1989 | Van Broekhoven et al. | 528/392 |
| 4,868,282 | 9/1989 | Van Broekhoven et al. | 528/392 |
| 4,880,903 | 11/1989 | Van Broekhoven et al. | 528/392 |

FOREIGN PATENT DOCUMENTS

| | | |
|---|---|---|
| 121965 | of 1984 | European Pat. Off. . |
| 181014 | of 1986 | European Pat. Off. . |
| 213671 | of 1986 | European Pat. Off. . |
| 257663 | of 1987 | European Pat. Off. . |
| 1081304 | of 1967 | United Kingdom . |

*Primary Examiner*—Patrick P. Garvin

[57] ABSTRACT

An improved process for the production of linear alternating polymers of carbon monoxide and at least one ethylenically unsaturated hydrocarbon comprises contacting the carbon monoxide and hydrocarbon under polymerization conditions in the presence of a reaction diluent and a novel catalyst composition formed from a palladium compound, a strong non-hydrohalogenic acid and a tetradentate aromatic phosphine ligand. The polymer products are of higher molecular weight and are produced at a faster rate than the more conventional process employing a catalyst composition formed from a bidentate ligand.

8 Claims, No Drawings

POLYMERIZATION PROCESS

This is a division, of application Ser. No. 07/503,414, filed Mar. 30, 1990 and now, U.S. Pat. No. 5,057,599.

FIELD OF THE INVENTION

This invention relates to the production of linear alternating polymers of carbon monoxide and at least one ethylenically unsaturated hydrocarbon. More particularly, the invention relates to an improved process for the production of such polymers and to novel catalyst compositions employed in the process.

BACKGROUND OF THE INVENTION

The class of polymers of carbon monoxide and olefin(s) has been known for some time. Brubaker, U.S. Pat. No. 2,495,286, produced such polymers of relatively low carbon monoxide content in the presence of free radical initiators, e.g., peroxy compounds. U.K. 1,081,304 produced similar polymers of higher carbon monoxide content in the presence of alkylphosphine complexes of palladium salts as catalyst. Nozaki extended the reaction to produce linear alternating polymers in the presence of arylphosphine complexes of palladium moieties and certain inert solvents. See, for example, U.S. Pat. No. 3,694,412.

More recently, the class of linear alternating polymers of carbon monoxide and at least one ethylenically unsaturated hydrocarbon has become of greater interest in part because of the greater availability of the polymers. The more recent processes for the production of such polymers, now known as polyketone polymers or polyketones, are illustrated by a number of published European Patent Applications including 121,965, 181,014, 213,671 and 257,663. The processes generally involve a catalyst composition formed from a compound of palladium, cobalt or nickel, the anion of a strong non-hydrohalogenic acid and a bidentate ligand of phosphorous, arsenic, antimony or nitrogen. The scope of the polymerization is extensive but, without wishing to be limited, a preferred catalyst composition has typically been formed from a compound of palladium, the anion of a non-hydrohalogenic acid having a pKa below about 6 and a bidentate ligand of phosphorus. The resulting polyketone polymers are thermoplastic materials of a relatively high molecular weight and are processed by methods conventional for thermoplastics into a variety of shaped articles of established utility.

In the production of the linear alternating polymers, both the rate of polymerization and the molecular weight of the polymer are important from economic considerations. A higher rate of reaction will, of course, produce more polymer per unit time. For many applications of the polyketone polymers the products of higher molecular weight are more useful. Unfortunately, the increased reaction temperatures which facilitate higher reaction rates generally result in polymer product of lower molecular weight. In practice, the reaction temperature is often selected to obtain polymer of the desired molecular weight and whatever reaction rate which results from that reaction temperature must be accepted. It would be of advantage to provide a process for the production of linear alternating polymers of carbon monoxide and at least one ethylenically unsaturated hydrocarbon which proceeds at an acceptable reaction rate but produces polymer product of an acceptable molecular weight.

SUMMARY OF THE INVENTION

The present invention provides an improved process for the production of linear alternating polymers of carbon monoxide and at least one ethylenically unsaturated hydrocarbon. More particularly, the invention provides a process for the production of such linear alternating polymers in the presence of certain novel catalyst compositions formed from, inter alia, a tetradentate ligand of phosphorus. The invention also relates to the novel catalyst compositions.

DESCRIPTION OF THE INVENTION

The polyketone polymers which are produced by the improved process of the invention are linear alternating polymers of carbon monoxide and at least one ethylenically unsaturated hydrocarbon. Suitable ethylenically unsaturated hydrocarbons which are useful as precursors of the linear alternating polymers have up to 20 carbon atoms inclusive, preferably up to 10 carbon atoms inclusive, and are aliphatic such as ethylene and other α-olefins including propylene, 1-butene, isobutylene, 1-hexene, 1-octene and 1-dodecene, or are arylaliphatic containing an aryl substituent on an otherwise aliphatic molecule, particularly an aryl substituent on a carbon atom of the ethylenic unsaturation. Illustrative of this latter class of ethylenically unsaturated hydrocarbons are styrene, p-methylstyrene, p-ethylstyrene and m-isopropylstyrene. Preferred polyketone polymers are copolymers of carbon monoxide and ethylene or terpolymers of carbon monoxide, ethylene and a second ethylenically unsaturated hydrocarbon of at least 3 carbon atoms, particularly an α-olefin such as propylene.

The structure of the polyketone polymers is that of a linear alternating polymer and the polymer contains substantially one molecule of carbon monoxide for each molecule of hydrocarbon. When the preferred terpolymers are produced according to the invention there will be at least about 2 units incorporating a moiety of ethylene for each unit incorporating a moiety of the second hydrocarbon. Preferably, there will be from about 10 units to about 100 units incorporating a moiety of ethylene for each unit incorporating a moiety of the second hydrocarbon. The polymer chain is therefore represented by the repeating formula

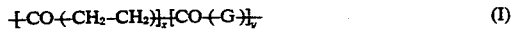 (I)

wherein G is the moiety of the second ethylenically unsaturated hydrocarbon polymerized through the ethylenic unsaturation thereof and the ratio of y:x is no more than about 0.5. When the preferred copolymers are produced there will be no second hydrocarbon present and the copolymers are represented by the above formula I wherein y is zero. When y is other than zero, i.e., terpolymers are produced, the —CO+(CH$_2$C-H$_2$)— units and the —CO+(G)— units will be found randomly throughout the polymer chain and the preferred ratios of y:x are from about 0.01 to about 0.1. The end groups or "caps" of the polymer chain will depend upon what materials were present during the polymerization and how or whether the polymer was purified. However, the precise nature of the end groups does not appear to influence the properties of the polymer to any considerable extent so that the polymer is fairly represented by the formula for the polymer chain as depicted above.

Of particular interest are the polymers of the above formula I of number average molecular weight from about 1000 to about 200,000, particularly those of molecular weight from about 20,000 to about 90,000, as determined by gel permeation chromatography. The physical properties of the polymer will depend in part on the molecular weight of the polymer, whether the polymer is a copolymer or a terpolymer and, in the case of a terpolymer, the nature of and the proportion of the second hydrocarbon present. Typical melting points for polyketone polymers produced according to the invention are from about 175° C. to about 300° C., more often from about 210° C. to about 270° C. The polymers will have a limiting viscosity number (LVN), measured in a standard capillary viscosity measuring device in m-cresol at 60° C., of from about 0.5 dl/g to about 10, but the preferred polymers have limiting viscosity numbers from about 0.8 dl/g to about 4 dl/g.

The present polymerization process employs a catalyst composition formed from a palladium compound, a non-hydrohalogenic acid having a pKa less than about 6, preferably less than 2, and a tetradentate ligand of phosphorus. The palladium compound is preferably a palladium alkanoate and palladium compounds such as palladium acetate, palladium propionate, palladium butyrate and palladium hexanoate are satisfactory. Particularly preferred as the palladium compound is palladium acetate. The preferred anion is the anion of a non-hydrohalogenic acid having a pKa below 2 (as measured in water at 18° C.). Acids which are suitable sources of anion include oxygen-containing inorganic acids such as sulfuric acid and perchloric acid and organic acids including carboxylic acids such as trichloroacetic acid, dichloroacetic acid and trifluoroacetic acid as well as sulfonic acids such as p-toluenesulfonic acid, methanesulfonic acid and trifluoromethanesulfonic acid. The acids trifluoroacetic acid and p-toluenesulfonic acid are particularly preferred, especially trifluoroacetic acid. The anion is preferably provided to the catalyst composition as the free acid but alternatively the anion is provided as a metal salt, particularly a non-noble transition metal salt such as a copper salt or a nickel salt. In yet another embodiment part or all of the anion is provided as the palladium salt, e.g., palladium trifluoroacetate. However provided, the anion is supplied in a quantity of from about 1 mol to about 1000 mols per mol of palladium. Preferred quantities of anion are from about 2 mols to about 100 mols per mol of palladium.

The tetradentate ligand of phosphorus is a tetrakis(diarylphosphino) compound of up to 40 carbon atoms having 4 diarylphosphino groups as substituents in an organic molecule in which at least two carbon atoms separate phosphino groups. A variety of such tetrakis(diarylphosphino) compounds are known and are suitable. Illustrative of such compounds are those of the types listed below together with an illustrative method of synthesis.

A. A 1,2,3,4-tetrakis(diphenylphosphino)-1,3-butadiene produced by reaction of 1,2-bis(diphenylphosphino)acetylene with diphenylphosphine, B. N,N,N′,N′-tetrakis(diphenylphosphinomethyl)ethylenediamine which may be prepared by reacting ethylenediamine with formaldehyde and diphenylphosphine, C. N,N,N′,N′-tetrakis(diphenylphosphinomethyl)hydrazine produced by reacting hydrazine with diphenylhydroxymethylphosphine, D. tetrakis(diphenylphosphinomethyl)methane produced by halogenating pentaerythritol and reacting the resulting tetrahalide with sodium diphenylphosphide, E. the tetrakis compound obtained by brominating durene with N-bromosuccinimide and reaction of the resulting tetrabromo compound with sodium diphenylphosphide, F. the tetrakis compound obtained by reacting 2-hydroxy-1,3-(diphenylphosphino)propane with terephthaloyl dichloride, G. the tetrakis compound obtained by reacting 2-hydroxy-1,3-bis(diphenylphosphino)propane with 4,4′-diisocyanatodiphenylmethane, H. the tetrakis compound obtained by reacting 2-hydroxy-1,3-bis(diphenylphosphino)propane with the diglycidyl ether of 2,2-di(4-hydroxyphenyl)propane, I. the tetrakis compound obtained by reacting 2-hydroxy-1,3-bis(diphenylphosphino)propane with 1,4-di(chloromethyl)benzene, J. the tetrakis compound obtained by reacting 1,4-di[(2-chloromethyl-3-chloro)propyl]benzene with an alkali metal diarylphosphide.

The preferred tetrakis(diarylphosphino) compounds are those of the formula

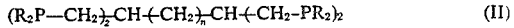

$$(R_2P-CH_2)_2CH+(CH_2)_n\!-\!CH+(CH_2-PR_2)_2 \qquad (II)$$

wherein R independently is aryl of up to 10 carbon atoms inclusive including hydrocarbyl aryl such a phenyl, tolyl, xylyl or naphthyl, or substituted-hydrocarbyl containing substituents having atoms other than carbon or hydrogen, particularly in the form of polar substituents at least one of which is located in a ring position ortho to the carbon atom through which the aryl group is connected to a phosphorus. The preferred polar substituents are alkoxy groups and illustrative substituted-hydrocarbyl aryl groups include 2-methoxyphenyl, 2-ethoxyphenyl, 2,4-dimethoxyphenyl, 2,6-diethoxyphenyl and 2,4,6-trimethoxyphenyl. The R groups phenyl and 2-methoxyphenyl are particularly preferred. In the above formula II the term "n" is an integer from 0 to about 14 inclusive but preferably is an integer from 0 to about 10.

The tetrakis(diarylphosphino) compounds of formula II are novel compounds although they are most easily produced by conventional methods such as by reacting the corresponding alcohol, a tetraol, with a sulfonic acid chloride such as p-toluenesulfonic acid chloride to produce the tetra sulfonic acid ester and subsequent reaction of the tetraester with an alkali metal diarylphosphide. The tetrakis(diarylphosphino) compound is employed in a quantity from about 0.25 mol to about 25 mols per mol of palladium but preferably in an amount from about 0.5 mol to about 10 mols per mol of palladium.

In order to enhance catalytic activity it is useful on occasion to additionally provide to the catalyst composition solution an organic oxidant. Suitable oxidants include quinones, both 1,2-quinones and 1,4-quinones, organic nitrites such as butyl nitrite and organic nitro compounds such as nitrobenzene and 2,4-dinitrotoluene. The preferred organic oxidants are the quinones, particularly 1,4-quinones such as 1,4-benzoquinone, 1,4-naphthoquinone and 1,4-anthraquinone. Especially preferred is 1,4-benzoquinone. As previously stated the provision of organic oxidant is not required and amounts of oxidant up to about 10,000 mols per mol of palladium are satisfactory. When oxidant is employed, amounts of oxidant from about 10 mols to about 5000 mols per mol of palladium are preferred.

The polymerization process of the invention is conducted by contacting the carbon monoxide and hydrocarbon reactants under polymerization conditions in the liquid phase in the presence of a reaction diluent. Alkanols are suitably utilized as reaction diluents, e.g., methanol and ethanol. Methanol is preferred. The contacting takes place in a suitable reactor and is more efficient if some means of agitation such as shaking or stirring is provided. The molar ratio of carbon monoxide to total ethylenically unsaturated hydrocarbon is from about 10:1 to about 1:10 but preferably is from about 5:1 to about 1:5. Sufficient catalyst composition is employed to provide from about $1 \times 10^{-7}$ mol to about $1 \times 10^{-3}$ mol of palladium, preferably from about $1 \times 10^{-6}$ mol to about $1 \times 10^{-4}$ mol of palladium, per mol of olefinically unsaturated hydrocarbon.

Typical polymerization conditions include a reaction temperature from about 25° C. to about 150° C., but reaction temperatures from about 30° C. to about 130° C. are more commonly utilized. The reaction pressure is suitably from about 2 bar to about 150 bar but is preferably from about 5 bar to about 100 bar. At the conclusion of polymerization the reaction is terminated as by cooling the reactor and releasing the pressure. The polymer product is customarily obtained as a material substantially insoluble in the reaction diluent and is recovered by conventional procedures such as filtration or decantation. The polymer is used as obtained or is purified as by contact with a solvent or extraction agent which is selective for catalyst residues.

The process of the invention provides the improvement of a faster reaction rate and a higher molecular weight (as reflected in a higher LVN) for the polymer product as compared with related processes employing a bidentate phosphine ligand. This improvement appears to be particular to process wherein the catalyst composition is formed from, inter alia, a tetradentate phosphine ligand. A corresponding process employing a catalyst composition formed from a tridentate does not provide a similar improvement and in general is inferior to the process employing a catalyst composition formed from a bidentate ligand. The polymer product finds utility as a premium thermoplastic and is converted to films, sheets, wires and shaped articles by methods which are conventional for thermoplastics, e.g., extrusion, injection molding and thermoforming. Particular applications for the polymer product include containers for food and drink and parts and housings for automotive applications.

The invention is further illustrated by the following Comparative Examples (not of the invention) and the following Illustrative Embodiments which should not be regarded as limiting. The polymer products of the Comparative Examples and the Illustrative Embodiments were examined by $^{13}$C-NMR. All copolymer products were found to be linear alternating copolymers of carbon monoxide and ethylene and all terpolymer products were found to be linear alternating terpolymers of carbon monoxide and ethylene or propylene. The limiting viscosity numbers were determined in m-cresol at 60° C.

COMPARATIVE EXAMPLE I

A copolymer of carbon monoxide and ethylene was produced by charging 200 ml of methanol to an autoclave of 300 ml capacity equipped with a mechanical stirrer. When the contents of the autoclave were brought to 85° C., an equimolar mixture of carbon monoxide and ethylene was introduced until a pressure of 55 bar was reached. A catalyst composition solution was then added which comprised 6 ml methanol, 0.01 mmol palladium acetate, 0.02 mmol trifluoroacetic acid and 0.01 mmol of 1,3-bis(diphenylphosphino)propane. The pressure within the autoclave was maintained at 55 bar by continuing addition of the equimolar gaseous mixture. After 4.7 hours the polymerization was terminated by cooling the reactor and contents to ambient temperature and releasing the pressure. The copolymer product was recovered by filtration, washed with methanol and dried at 70° C.

The yield of copolymer was 30 g, produced at a rate of 6.0 kg copolymer/g pd hr. The LVN of the polymer was 0.8 dl/g.

COMPARATIVE EXAMPLE II

A carbon monoxide/ethylene copolymer was produced by a procedure substantially similar to that of Comparative Example I except the catalyst composition contained 1,3-bis(diphenylphosphino)-2-methyl-2-diphenylphosphinomethylpropane instead of 1,3-bis(diphenylphosphino)propane and the reaction time was 6.6 hours instead of 4.7 hours.

The yield of copolymer was 26 g produced at a rate of 3.7 kg copolymer/g Pd hr. The LVN of the polymer was 0.4 dl/g.

COMPARATIVE EXAMPLE III

A terpolymer of carbon monoxide, ethylene and propylene was produced by charging 200 ml of methanol and 24 ml of liquid propylene to an autoclave of 300 ml capacity equipped with a mechanical stirrer. The contents of the autoclave were warmed to 87° C. and an equimolar mixture of carbon monoxide and ethylene was added until a pressure of 56 bar was reached. A catalyst composition solution was then added which comprised 6 ml methanol, 0.01 mmol palladium acetate, 0.2 mmol trifluoroacetic acid and 0.01 mmol 1,3-bis(diphenylphosphino)propane. The pressure was maintained at 56 bar by continuing addition of the equimolar mixture. After 3.7 hours the polymerization was terminated by cooling the autoclave and contents to ambient temperature and releasing the pressure. The terpolymer was recovered by filtration, washed with methanol and dried at 70° C.

The yield of terpolymer was 21 g, produced at a rate of 5.3 g terpolymer/g Pd hr. The LVN of the terpolymer was 0.4 dl/g.

COMPARATIVE EXAMPLE IV

A terpolymer of carbon monoxide, ethylene and propylene was produced by a procedure substantially similar to that of Comparative Example III except that the catalyst composition solution contained 1,3-bis(diphenylphosphino)-2-methyl-2-diphenylphosphinomethylpropane instead of 1,3-bis(diphenylphosphino)propane and the reaction time was 6.1 hours instead of 3.7 hours.

The yield of terpolymer was 18 g produced at a rate of 2.8 kg terpolymer/g Pd hr. The LVN of the terpolymer was 0.4 dl/g.

COMPARATIVE EXAMPLE V

A copolymer of carbon monoxide and ethylene was produced by charging 200 ml of methanol to an autoclave of 300 ml capacity equipped with a mechanical stirrer. The contents of the autoclave were heated to 90° C. and an equimolar mixture of carbon monoxide and ethylene was added until a pressure of 55 bar was reached. A catalyst composition solution was then added which comprised 4.5 ml of methanol, 1.5 ml of toluene, 0.01 mmol palladium acetate, 0.2 mmol trifluoroacetic acid and 0.012 mmol of 1,3-bis[di(2-methoxyphenyl)phosphino]propane. The pressure in the autoclave was maintained at 55 bar by continued addition of the equimolar mixture. After 2.58 hours the polymerization was terminated by cooling the autoclave and contents to ambient temperature and releasing the pressure. The copolymer was recovered as described above.

The yield of copolymer was 6.22 g produced at a rate of 2.3 kg copolymer/g Pd hr. The LVN of the copolymer was 1.3 dl/g.

ILLUSTRATIVE EMBODIMENT I

A carbon monoxide/ethylene copolymer was produced by a procedure substantially similar to that of Comparative Example V except that the catalyst composition comprised 6 ml of acetone, 0.01 mmol palladium acetate, 0.2 mmol trifluoroacetate and 0.005 mmol 1,8-bis[di(2-methoxyphenyl)phosphino]-2,7-bis[di(2-methoxyphenyl)phosphinomethyl]octane and the reaction time was 1.7 hours instead of 2.58 hours.

The yield of copolymer was 8.0 g produced at a rate of 9.5 kg copolymer/g Pd hr. The LVN of the copolymer was 1.8 dl/g.

COMPARATIVE EXAMPLE VI

A terpolymer of carbon monoxide, ethylene and propylene was produced by charging 178 ml of methanol and 24 g of propylene to an autoclave of 300 ml capacity equipped with a mechanical stirrer. The autoclave and contents were heated to 80° C. and an equimolar mixture of carbon monoxide and ethylene was added until a pressure of 55 bar was reached. A catalyst composition solution was then added which comprised 4.5 ml methanol, 1.5 ml toluene, 0.01 mmol palladium acetate, 0.2 mmol trifluoroacetic acid and 0.011 mmol 1,3-bis[di(2-methoxyphenyl)phosphino]-propane. The pressure within the reactor was maintained by continued addition of the equimolar mixture. After 2.45 hours the polymerization was terminated and the polymer recovered as before.

The yield of terpolymer was 8.9 g produced at a rate of 3.4 kg terpolymer/g Pd hr. The LVN of the terpolymer was 2.1 dl/g.

ILLUSTRATIVE EMBODIMENT II

A carbon monoxide/ethylene/propylene terpolymer was produced by a procedure substantially similar to that of Comparative Example VI except that the catalyst composition solution comprised 4.5 ml methanol, 1.5 ml toluene, 0.009 mmol palladium acetate, 0.2 mmol trifluoroacetic acid and 0.005 mmol of 1,8-bis[di(2-methoxyphenyl)phosphino]-2,7-bis[di(2-methoxyphenyl)phosphinomethyl]octane and the reaction time was 1.92 hours instead of 2.45 hours.

The yield of terpolymer was 20.3 g produced at a rate of 11.1 kg terpolymer/g pd hr. The LVN of the terpolymer was 2.6 dl/g.

COMPARATIVE EXAMPLE VII

A carbon monoxide/ethylene copolymer was produced by charging 1.5 liter of methanol to an autoclave of 3.8 liter capacity equipped with a mechanical stirrer. After the contents of the autoclave were heated to 80° C., ethylene was introduced to give an ethylene partial pressure of 7.6 bar and carbon dioxide was introduced to give a carbon monoxide partial pressure of 11.4 bar. A catalyst composition solution was then introduced which comprised 6 ml acetone, 0.02 mmol palladium acetate, 0.4 mmol trifluoroacetic acid and 0.024 mmol 1,3-bis[di(2-methoxyphenyl)phosphino]-propane. The pressure in the autoclave was maintained by addition of an equimolar mixture of carbon monoxide and ethylene. After 19 hours the polymerization was terminated by cooling the autoclave and contents to ambient temperature and releasing the pressure. The copolymer was recovered by filtration, washed with methanol and dried at 70° C.

The yield of copolymer was 97 g produced at a rate of 2.4 kg copolymer/g Pd hr. The LVN of the copolymer was 2.1 dl/g.

ILLUSTRATIVE EMBODIMENT III

A copolymer of carbon monoxide and ethylene was produced by a procedure substantially similar to that of Comparative Example VII except that the catalyst composition solution contained 1,8-bis[di(2-methoxyphenyl)phosphino]-2,7-bis[di(2-methoxyphenyl)phosphinomethyl)octane instead of 1,3-bis[di(2-methoxyphenyl)phosphino]propane and the reaction time was 17 hours instead of 19 hours.

The yield of copolymer was 90 g produced at a rate of 2.5 kg of copolymer/g Pd hr. The LVN of the copolymer was 2.7 dl/g.

COMPARATIVE EXAMPLE VIII

A carbon monoxide/ethylene/propylene terpolymer was produced by a procedure substantially similar to that of Comparative Example VII except that a) quantities of ethylene, propylene and carbon monoxide were added to the autoclave to give partial pressures of 8.5 bar, 7 bar and 23.5 bar respectively.

b) The reaction temperature was 75° C. instead of 80° C., and c) the reaction time was 23 hours instead of 19 hours.

The yield of terpolymer was 170 g produced at a rate of 3.5 kg of terpolymer/g Pd hr. The LVN of the terpolymer was 1.9 dl/g.

ILLUSTRATIVE EMBODIMENT IV

A carbon monoxide/ethylene/propylene terpolymer was produced by a procedure substantially similar to that of Comparative Example VIII except that the catalyst composition solution contained 0.012 mmol of 1,8-bis[di(2-methoxyphenyl)phosphino]2,7-bis[di(2-methoxyphenyl)phosphinomethyl]octane and the reaction time was 4.5 hours instead of 23 hours.

The yield of terpolymer was 40 g produced at a rate of 4.2 kg terpolymer/g Pd hr. The LVN of the terpolymer was 3.1 dl/g.

What is claimed is:

1. A catalyst composition formed from a palladium compound, the anion of a non-hydrohalogenic acid having a pKa below 2 and an aromatic tetradentate phosphine ligand of up to 40 carbon atoms and 4 diarylphosphino substituents in a molecule wherein at least two carbon atoms separate phosphino groups.

2. The catalyst composition of claim 1 wherein the phosphine ligand is of the formula $$(R_2P-CH_2)_2CH-CH_2)_nCH-CH_2-PR_2)_2$$

wherein n is an integer from 0 to about 14 and R independently is aryl of up to 10 carbon atoms.

3. The catalyst composition of claim 2 wherein the palladium compound is a palladium alkanoate.

4. The catalyst composition of claim 3 wherein the anion is the anion of trifluoroacetic acid or p-toluenesulfonic acid.

5. The catalyst composition of claim 4 wherein R independently is phenyl or 2-methoxyphenyl.

6. The catalyst composition of claim 5 wherein the palladium alkanoate is palladium acetate.

7. The catalyst composition of claim 6 wherein R is phenyl.

8. The catalyst composition of claim 7 wherein R is 2-methoxyphenyl.

* * * * *